United States Patent
Cheng et al.

(10) Patent No.: US 11,000,569 B2
(45) Date of Patent: *May 11, 2021

(54) MEDICAMENT FOR USE IN TREATING FATTY LIVER, HEPATITIS AND CIRRHOSIS

(71) Applicant: Shandong Zhonghai Pharmaceutical CO. LTD, Weifang (CN)

(72) Inventors: Qian Cheng, Weifang (CN); Baozhen Xu, Weifang (CN); Long Cheng, Weifang (CN)

(73) Assignee: SHANDONG ZHONGHAI PHARMACEUTICAL CO. LTD, Weifang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/073,860

(22) PCT Filed: Jan. 20, 2017

(86) PCT No.: PCT/CN2017/071837
§ 371 (c)(1),
(2) Date: Jul. 30, 2018

(87) PCT Pub. No.: WO2017/129055
PCT Pub. Date: Aug. 3, 2017

(65) Prior Publication Data
US 2019/0038708 A1   Feb. 7, 2019

(30) Foreign Application Priority Data
Jan. 29, 2016   (CN) .......................... 201610061775.9

(51) Int. Cl.
| | | |
|---|---|---|
| *A61K 38/16* | (2006.01) |
| *A61K 31/715* | (2006.01) |
| *A61P 1/16* | (2006.01) |
| *A61K 31/7012* | (2006.01) |
| *A61K 36/05* | (2006.01) |
| *A61K 36/752* | (2006.01) |
| *A61K 36/315* | (2006.01) |
| *A61K 36/02* | (2006.01) |
| *A61K 36/03* | (2006.01) |
| *A61K 36/04* | (2006.01) |
| *A61K 36/896* | (2006.01) |
| *A61K 31/4025* | (2006.01) |

(52) U.S. Cl.
CPC ........ *A61K 38/168* (2013.01); *A61K 31/4025* (2013.01); *A61K 31/7012* (2013.01); *A61K 31/715* (2013.01); *A61K 36/02* (2013.01); *A61K 36/03* (2013.01); *A61K 36/04* (2013.01); *A61K 36/05* (2013.01); *A61K 36/315* (2013.01); *A61K 36/752* (2013.01); *A61K 36/896* (2013.01); *A61P 1/16* (2018.01)

(58) Field of Classification Search
CPC ... A61K 38/168; A61K 36/05; A61K 31/7012
See application file for complete search history.

(56) References Cited

U.S. PATENT DOCUMENTS

2013/0101514 A1 *  4/2013  Cushing ............... A61K 31/201
424/9.1

FOREIGN PATENT DOCUMENTS

| CN | 1844259 A | 10/2006 |
|---|---|---|
| CN | 101481393 A | 7/2009 |
| CN | 101703710 A * | 5/2010 |
| CN | 101760492 A | 6/2010 |
| CN | 102077933 A * | 6/2011 |
| CN | 102078543 A * | 6/2011 |
| CN | 102417544 A * | 4/2012 |
| CN | 102430099 A | 5/2012 |
| CN | 102824600 A * | 12/2012 |
| CN | 102861245 A * | 1/2013 |
| CN | 105709206 A | 6/2016 |

OTHER PUBLICATIONS

Hwang et al. Food and Chemical Toxicology 46 (2008) 3475-3481. (Year: 2008).*
Jung et al. Arch Pharm Res 27(2), 2004, pp. 184-188. (Year: 2004).*

* cited by examiner

*Primary Examiner* — Amy L Clark
(74) *Attorney, Agent, or Firm* — Bayramoglu Law Offices LLC

(57) ABSTRACT

A medicament for use in treating fatty liver, hepatitis and cirrhosis, the medicament includes a marine algal glycoprotein.

1 Claim, No Drawings

MEDICAMENT FOR USE IN TREATING FATTY LIVER, HEPATITIS AND CIRRHOSIS

CROSS REFERENCE TO RELATED APPLICATIONS

This application is the national phase entry of International Application No. PCT/CN2017/071837, filed on Jan. 20, 2017, which is based upon and claims priority to Chinese Patent Application No. 201610061775.9, filed on Jan. 29, 2016, the entire contents of which are incorporated herein by reference.

TECHNICAL FIELD

The present invention relates to a medicament for use in treating fatty liver, hepatitis and cirrhosis, which belongs to the technical field of medical technology.

BACKGROUND

Infection rate of hepatitis B virus in China is approximate 60%-70%. Hepatitis B surface antigen carrying rate takes account of 7.18% of total population, based on which it is estimated that about 93 million people carry hepatitis B virus, among of which 30 million are hepatitis B patients. Currently, patients who have jaundice hepatitis A, hepatitis disease, virus and HBE are found everywhere. There are many reason for cause or induction of jaundice hepatitis A, hepatitis B viral, such as excessive drinking, low body immunity, irregular eating. For patients with liver disease, they are discriminated to varying degrees in terms of family affection, marital love, school attendance, employment, going abroad and social intercourses. Their lives are inevitably covered with sad colors. Currently, there is no method to cure hepatitis virus, but only relieve it. Patients has to take medicines for long time which is not only troublesome, but also expensive. Furthermore, it is easy to recur.

At present, there is no specific medicine to treat chronic hepatitis B, hepatitis C and liver cirrhosis. The interferon commonly-used in present has certain effect on chronic hepatitis B, hepatitis C and liver cirrhosis. For instance, its response rate is only at 15%-20% for treatment of hepatitis C (Effect Research of Interferon on Hepatitis C: Chinese Journal of Integrated Traditional and Western Medicine on Liver Disease, volume 2002-12, 1st issue, page 56); however, big side effect, high recurrence rate and expensive price make the interferon not conforming with Chinese medical consumption level.

SUMMARY

The present invention provides a medicament for use in treating fatty liver, hepatitis and cirrhosis in order to solve the deficiencies in the prior art for the purpose to achieve the following objectives hereof:

(1) The medicament in the present invention has good therapeutic effect on hepatitis. After 3-month therapy, ALT is reduced to 41.5-45.9 IU/L, TbiL is reduced to 37.3-42.6 μmol/L, Alb is reduced to 32.6-35.0 g/L, HBV-DNA is reduced to 4.0-4.9 copy/mL, HbeAg negative rate is 75-82% and HBV-DNA negative rate is 83-87%.

(2) The medicament in the present invention has good therapeutic effect on liver cirrhosis. After 3-month therapy, ALT is reduced to 38.5-42.3 IU/L, TbiL is reduced to 45.0-48.6 μmol/L, Alb is reduced to 26.6-30.5 g/L, portal vein diameter is reduced to 14.0-15.1 mm, splenic vein diameter is reduced to 8.0-8.5 mm and spleen thickness is reduced to 48.5-49.2 mm.

(3) The medicament in the present invention has high curative rate in treat of hepatitis and liver cirrhosis in whole and its total effective rate reaches to 89.9-92.5%.

In order to solve the above technical problems, the present invention adopts the following technical solution:

A medicament for use in treating fatty liver, hepatitis and cirrhosis, wherein the medicament is a glycoprotein, a mixture of polysaccharide and protein, a polypeptide or a protein; the glycoprotein comprises 1%-99% of sugar and 1%-99% of protein; the mixture of polysaccharide and protein comprises 1%-99% of sugar and 1%-99% of protein by weight. The molecular weight of the glycoprotein is 0.2-3000 kDa.

The following are further modifications to the above technical solution:

the medicament is a marine algal glycoprotein;
the marine algal glycoprotein comprises 1%-99% of sugar and 1%-99% of protein by weight; the mixture of marine algal polysaccharide and protein comprises 1%-99% of sugar and 1%-99% of protein by weight.

The marine algal glycoprotein has a molecular weight of 0.2-3000 kDa;
as for the mixture of polysaccharide and protein, the polysaccharide has a molecular weight of 0.2-3000 kDa and the protein has a molecular weight of 0.2-3000 kDa.

The medicament comprises 1-99 portions of glycoprotein and 1-25 portions of glucuronic acid by weight.

The medicament comprises 1-99 portions of marine algal glycoprotein and 1-24 portions of glucuronic acid by weight.

The medicament comprises 1-99 portions of marine algal glycoprotein, 1-27 portions of glucuronic acid and 2-10 portions of indigo naturalis by weight.

The alga comprises one or more kinds of blue-green algae, green algae, red algae, -gold algae, and brown algae.

The medicament comprises 1-99 portions of marine algal glycoprotein, 8-14 portions of indigo naturalis, and 7-13 portions of *rhizoma belamcandae* and 1-15 portions of glucuronic acid by weight.

The medicament comprises 1-99 portions of marine algal glycoprotein, 8-14 portions of indigo naturalis, and 7-13 portions of *rhizoma belamcandae* and 8-12 portions of fructus aurantii by weight.

The medicament comprises 1%-99% of sugar and 1%-99% of protein by weight.

The marine algal glycoprotein comprises 1%-99% of sugar and 1%-99% of protein by weight.

Compared with the prior art, the advantages of the present invention are:

(1) The medicament in the present invention has good therapeutic effect on hepatitis. After 3-month therapy, ALT is 41.5-45.9 IU/L, TbiL is 37.3-42.6 μmol/L, Alb is 32.6-35.0 g/L, HBV-DNA is 4.0-4.9 copy/mL, HbeAg negative rate is 75-82% and HBV-DNA negative rate is 83-87%.

(2) The medicament in the present invention has good therapeutic effect on liver cirrhosis. After three months treatment, ALT is 38.5-42.3 IU/L, TbiL is 45.0-48.6 μmol/L, Alb is 26.6-30.5 g/L, portal vein diameter is 14.0-15.1 mm, splenic vein diameter is 8.0-8.5 mm and spleen thickness is to 48.5-49.2 mm.

(3) The medicament in the present invention has high curative ratio in treating hepatitis and liver cirrhosis in whole with a total effective rate is 89.9-92.5%.

DETAILED DESCRIPTION OF THE EMBODIMENTS

The preferred embodiments of the present invention are described in the following, and the preferred embodiments described herein are only intended to illustrate and explain the invention, but not limited to this invention.

Embodiment 1

Medicament For Use in Treating Fatty Liver, Hepatitis and Cirrhosis

The medicament mentioned is a marine algal glycoprotein:
The marine algae glycoproteins comprises 1% sugar and 99% protein by weight;
and the molecular weight is 0.2 kDa;
the marine algae is blue-green algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 2

Medicament For Use in Treating Fatty Liver, Hepatitis and Cirrhosis

Wherein the medicament is a marine algal glycoprotein;
the marine algal glycoproteins comprises 12%-sugar and 85% protein by weight;
the molecular weight is 28 kDa;
the marine algae is green algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 3

Medicament For Use in Treating Fatty Liver, Hepatitis and Cirrhosis

Wherein the medicament is a marine algal glycoprotein;
the marine algae glycoproteins comprises 35% sugar and 64% protein by weight;
and the molecular weight is 68 kDa;
the marine algae is red algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 4

Medicament For Use in Treating Fatty Liver, Hepatitis and Cirrhosis

Wherein the medicament is a marine algal glycoprotein;
the marine algae glycoproteins comprises 55% sugar and 40% protein by weight;
the molecular weight is 5 kDa;
the marine algae is blue-green algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 5

Medicament For Use in Treating Fatty Liver, Hepatitis and Cirrhosis

Wherein the medicament is a marine algal glycoprotein;
the marine algae glycoproteins comprises 77% sugar and 23% protein by weight;
and the molecular weight is 600 kDa;
the marine algae is brown algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 6

Medicament For Use in Treating Fatty Liver, Hepatitis and Cirrhosis

Wherein the medicament is a marine algal glycoprotein;
the marine algae glycoproteins comprises 99% sugar and 1% protein by weight;
and the molecular weight is 3000 kDa;
the marine algae is gold algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

The glycoprotein in these above Embodiments 1-6 further includes a pigment; the pigment is a natural pigment contained in the algal substances;

These above Embodiments 1-6 could be summarized as: Medicament For Use in Treating Fatty Liver, Hepatitis and Cirrhosis The medicament is a glycoprotein;
the glycoprotein comprises 1%-99% of sugar and 1%-99% of protein by weight;
the molecular weight is 0.2-30000 kDa;
the sugar is a polysaccharide;
the medicament includes synthetic glycoproteins and synthetic polysaccharides and proteins.

The protein comprises 20 kinds of amino acids and 8 kinds of synthetic amino acids; the preparation method of the medicament: the glycoprotein is prepared into capsules and tablets etc. according to a conventional process; the mixture of the polysaccharide and the protein is prepared into capsules and tablets etc. according to a conventional process.

Embodiment 7

Application of the Medicament in Treating Fatty Liver, Hepatitis and Cirrhosis

Case selection: patients with chronic hepatitis B and posthepatitic cirrhosis are selected. 420 patients are in treatment group, including 210 patients with chronic hepatitis (including mild, moderate and severe) aging from 18-78, average age of (39±7.9), 210 patients with posthepatitic cirrhosis aging from 30-74 at average age of (45±12). All these patients are caused by hepatitis B virus and grouped into 20.

60 patients are in control group, including 31 patients with chronic hepatitis B (24 male and 27 female) aging from 18-60 at average of (32.7±7.3), 29 patients with liver cirrhosis (23 male and 6 female) aging from 29-74 at average age of (44±10). Patient age, gender condition and state of illness for both treatment group and control group are similar and comparable ((P>0.05).

Treatment method: For patients in treatment group were administered the medicament in the invention implementation Embodiments 1-6 and Embodiments 8-22 at a dose of 3 g/day, three times a day. A period of treatment is three consecutive months.

Control group: liver-protecting tablet is given with a dose of 5 tablets/day and 3 times/day. Period of treatment is the same with the above. Basic treatment for treatment and control group is the same.

Observation:

Pneumonia: Check ALT, TbiL, Alb, HBV-DNA, HBeAg negative rate, and HBV-DNA negative rate every month prior to and after treatment.

Liver cirrhosis: ALT, TbiL, Alb, portal vein diameter, splenic diameter, and spleen thickness.

Evaluation of therapeutic effect: markedly effective, Clinical symptoms (abdominal distension, liver area pain) disappear, normal liver function. Effecacy: improvement of clinical symptoms, improvement of liver function prior to treatment. Ineffecacy: no change of clinical symptoms and liver function.

Observe the effect after three months treatment.

TABLE 1

Therapeutic effect of the medicament in the invention on hepatitis

| | ALT IU/L | TbiL μmol/L | Alb g/L | HBV-DNA Copy/mL | HbeAg Negative conversion rate % | HBV-DNA Negative conversion rate % |
|---|---|---|---|---|---|---|
| Control group before treatment | 77.8 | 60.3 | 31.3 | 5.2 | | |
| Control group after treatment | 41.8 | 38.2 | 34.5 | 4.2 | 70 | 80 |
| Treatment group before treatment | 78.2 | 61.4 | 30.9 | 5.3 | | |
| Embodiment 1 | 45.9 | 42.6 | 32.6 | 4.9 | 75 | 83 |
| Embodiment 2 | 43.2 | 39.1 | 34.6 | 4.5 | 77 | 85 |
| Embodiment 3 | 41.5 | 37.3 | 35.0 | 4.1 | 80 | 87 |
| Embodiment 4 | 42.6 | 37.9 | 34.5 | 4.0 | 82 | 84 |
| Embodiment 5 | 43.5 | 38.4 | 34.0 | 4.5 | 79 | 83 |
| Embodiment 6 | 44.9 | 40.9 | 33.2 | 4.8 | 76 | 83 |

The medicament in the present invention has good therapeutic effect on hepatitis. After three months treatment, ALT is 41.5-45.9 IU/L, TbiL is 37.3-42.6 μmol/L, Alb is 32.6-35.0 g/L, HBV-DNA is 4.0-4.9 copy/mL, HbeAg negative rate is 75-82% and HBV-DNA negative rate is 83-87%.

TABLE 2

Therapeutic effect of the medicament in the invention on cirrhosis

| | ALT IU/L | TbiL μmol/L | Alb g/L | Portal vein diameter (mm) | Splenic vein diameter (mm) | Splenic thickness (mm) |
|---|---|---|---|---|---|---|
| Control group before treatment | 57.8 | 50.3 | 21.3 | 15.8 | 9.2 | 50.5 |
| Control group after treatment | 38.8 | 45.2 | 28.6 | 15.0 | 8.2 | 48.8 |
| Treatment group before treatment | 58.2 | 51.4 | 20.9 | 15.9 | 9.1 | 50 |
| Embodiment 1 | 42.3 | 48.6 | 26.6 | 15.1 | 8.5 | 49.2 |
| Embodiment 2 | 40.6 | 47.9 | 29.6 | 14.6 | 8.2 | 49.0 |
| Embodiment 3 | 38.5 | 45.0 | 30.5 | 14.0 | 8.0 | 48.5 |
| Embodiment 4 | 39.5 | 46.7 | 28.4 | 14.5 | 8.1 | 48.7 |
| Embodiment 5 | 40.6 | 46.9 | 27.9 | 14.9 | 8.3 | 48.9 |
| Embodiment 6 | 41.7 | 47.5 | 27.0 | 15.0 | 8.4 | 49.1 |

The medicament in the present invention has good therapeutic effect on liver cirrhosis. After 3-month treatment, ALT is 38.5-42.3 IU/L, TbiL is 45.0-48.6 μmol/L, Alb is 26.6-30.5 g/L, portal vein diameter is 14.0-15.1 mm, splenic vein diameter is 8.0-8.5 mm and spleen thickness is to 48.5-49.2 mm.

TABLE 3

Curative rate in whole of the medicament in the invention on fatty liver, hepatitis, liver cirrhosis

| | Markedly effective (rate %) | Effective (rate %) | Ineffective (rate %) | Total effective (rate %) |
|---|---|---|---|---|
| Embodiment 1 | 50.4 | 40.5 | 9.1 | 90.9 |
| Embodiment 2 | 51.6 | 40.2 | 8.2 | 91.8 |
| Embodiment 3 | 52.7 | 39.8 | 7.5 | 92.5 |
| Embodiment 4 | 51.7 | 40.5 | 7.8 | 92.2 |
| Embodiment 5 | 50.8 | 41.0 | 8.2 | 91.8 |
| Embodiment 6 | 50.5 | 39.4 | 10.1 | 89.9 |

The medicament in the invention has high curative rate in treating fatty liver, hepatitis and liver cirrhosis in whole with total effective rate reaches to 89.9-92.5%.

Embodiment 8

Medicament For Use in Treating Fatty Liver, Hepatitis and Cirrhosis

It comprises 1 portion of marine algal glycoprotein and 1 portion of glucuronic acid by weight.

The marine algal glycoprotein comprises, on the basis of weight, includes 11% sugar and 85% protein.

The molecular weight is 8 kDa;
the marine algae is spirulina;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 9

Medicament For Use in Treating Fatty Liver, Hepatitis and Cirrhosis

Like Embodiment 8, only the weight ratio of marine algal glycoprotein to glucuronic acid is changed as follows:

It comprises 25 portions of marine algal glycoprotein and 7 portions of glucuronic acid by weight.

Embodiment 10

Medicament For Use in Treating Fatty Liver, Hepatitis and Cirrhosis

Like Embodiment 8, only the weight ratio of marine algal glycoprotein to glucuronic acid is changed as follows:

It comprises 66 portions of marine algal glycoprotein and 13 portions of glucuronic acid by weight.

Embodiment 11

Medicament For Use in Treating Fatty Liver, Hepatitis and Cirrhosis

Like Embodiment 8, only the weight ratio of marine algal glycoprotein to glucuronic acid is changed as follows:

It comprises 99 portions of marine algal glycoprotein and 24 portions of glucuronic acid by weight.

Embodiment 12

Medicament For Use in Treating Fatty Liver, Hepatitis and Cirrhosis

It comprises 1 portion of marine algal glycoprotein, 1 portion of glucuronic acid and 2 portions of indigo naturalis by weight.

The marine algal glycoprotein comprises 23% sugar and 79% protein by weight.

The molecular weight is 35 kDa;
the glycoproteins in marine algae is the chlorella;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 13

Medicament For Use in Treating Fatty Liver, Hepatitis and Cirrhosis

Like Embodiment 12, only the weight ratio of marine algal glycoprotein, glucuronic acid and indigo naturalis is changed as follows:

It comprises 24 portions of marine algal glycoprotein, 9 portions of glucuronic acid and 5 portions of indigo naturalis by weight.

Embodiment 14

Medicament For Use in Treating Fatty Liver, Hepatitis and Cirrhosis

Like Embodiment 12, only the ratio of marine algal glycoprotein, glucuronic acid and indigo naturalis is changed as follows:

It comprises 53 portions of marine algal glycoprotein, 14 portions of glucuronic acid and 8 portions of indigo naturalis by weight.

Embodiment 15

Medicament For Use in Treating Fatty Liver, Hepatitis and Cirrhosis

Like Embodiment 12, only the ratio of marine algal glycoprotein, glucuronic acid and indigo naturalis is changed as follows:

It comprises 99 portions of marine algal glycoprotein, 27 portions of glucuronic acid and 10 portions of indigo naturalis by weight.

Application of the Medicament in Embodiments 8-15 in Treating Fatty Liver, Hepatitis and Cirrhosis Using the test method mentioned in Embodiment 7, the medicament has following applicable effects:

TABLE 4

Therapeutic effect of the medicament in the invention on hepatitis

| | ALT IU/L | TbiL μmol/L | Alb g/L | HBV-DNA Copy/mL | HbeAg Negative conversion rate % | HBV-DNA Negative conversion rate % |
|---|---|---|---|---|---|---|
| Control group before treatment | 77.8 | 60.3 | 31.3 | 5.2 | | |
| Control group after treatment | 41.8 | 38.2 | 34.5 | 4.2 | 70 | 80 |
| Treatment group before treatment | 78.2 | 61.4 | 30.9 | 5.3 | | |
| Embodiment 8 | 35.9 | 34.2 | 33.6 | 3.9 | 78 | 85 |
| Embodiment 9 | 33.2 | 35.1 | 34.7 | 3.5 | 80 | 86 |
| Embodiment 10 | 25.5 | 26.5 | 38.6 | 2.9 | 89 | 95 |
| Embodiment 11 | 32.6 | 36.9 | 35.5 | 3.6 | 82 | 84 |
| Embodiment 12 | 30.5 | 37.4 | 35.0 | 3.7 | 80 | 86 |
| Embodiment 13 | 31.9 | 35.9 | 35.2 | 3.8 | 81 | 85 |
| Embodiment 14 | 26.7 | 26.0 | 38.4 | 2.94 | 90 | 96 |
| Embodiment 15 | 32.5 | 36.5 | 35.7 | 3.5 | 83 | 84 |

TABLE 5

Therapeutic effect of the medicament in the invention on cirrhosis

| | ALT IU/L | TbiL μmol/L | Alb g/L | Portal vein diameter (mm) | Splenic vein diameter (mm) | Splenic thickness (mm) |
|---|---|---|---|---|---|---|
| Control group before treatment | 57.8 | 50.3 | 21.3 | 15.8 | 9.2 | 50.5 |
| Control group after treatment | 38.8 | 45.2 | 28.6 | 15.0 | 8.2 | 48.8 |
| Treatment group before treatment | 58.2 | 51.4 | 20.9 | 15.9 | 9.1 | 50 |
| Embodiment 8 | 38.3 | 45.6 | 30.6 | 14.2 | 8.1 | 48.2 |
| Embodiment 9 | 39.6 | 45.9 | 29.6 | 14.3 | 8.0 | 48.0 |
| Embodiment 10 | 34.5 | 39.0 | 35.5 | 13.4 | 7.5 | 46.5 |
| Embodiment 11 | 39.5 | 46.7 | 30.4 | 14.0 | 8.0 | 48.1 |
| Embodiment 12 | 38.6 | 44.9 | 29.9 | 14.2 | 8.1 | 48.2 |
| Embodiment 13 | 37.7 | 44.5 | 30.0 | 15.0 | 8.1 | 47.8 |
| Embodiment 14 | 33.6 | 38.4 | 35.9 | 13.3 | 7.4 | 46.2 |
| Embodiment 15 | 37.8 | 44.6 | 30.7 | 14.8 | 7.9 | 48.3 |

TABLE 6

Overall curative rate of the medicament in the invention on fatty liver, hepatitis, liver cirrhosis

| | Markedly effective (rate %) | Effective (rate %) | Ineffective (rate %) | Total effective (rate %) |
|---|---|---|---|---|
| Embodiment 8 | 50.4 | 41.5 | 8.1 | 91.9 |
| Embodiment 9 | 51.6 | 40.0 | 8.4 | 91.6 |
| Embodiment 10 | 55.7 | 39.8 | 4.5 | 95.5 |
| Embodiment 11 | 51.7 | 40.7 | 7.6 | 92.4 |
| Embodiment 12 | 50.8 | 41.0 | 8.2 | 91.8 |
| Embodiment 13 | 50.5 | 40.4 | 9.1 | 90.9 |
| Embodiment 14 | 54.7 | 40.8 | 4.5 | 95.5 |
| Embodiment 15 | 50.5 | 40.5 | 9.0 | 91.0 |

In Embodiments 8-11, only the weight ratio of the marine algal glycoprotein and glucuronic acid is changed. From the experimental results, Embodiment 10 is the most preferred embodiment;

in Embodiments 12-15, only the weight ratio of the marine algae glycoprotein, glucuronic acid and indigo naturalis is changed. From the experimental results, Embodiment 14 is the most preferred embodiment.

Embodiment 16

Medicament For Use in Treating Fatty Liver, Hepatitis and Cirrhosis

It comprises 1 portion of marine algal glycoprotein, 8 portions of indigo naturalis, 7 portions of *rhizoma belamcandae* and 1 portion of glucuronic acid by weight.

The marine algal glycoprotein comprises 26% sugar and 74% protein by weight.

The molecular weight is 8 kDa;

the marine algae is blue-green algae;

the sugar is a polysaccharide;

the polysaccharide comprises: xylose, fucose, arabinose, glucose, galactose, mannose and rhamnose;

the protein comprises: asparagine, cysteine, lysine, arginine, serine, threonine, glutamic acid.

Embodiment 17

Medicament For Use in Treating Fatty Liver, Hepatitis and Cirrhosis

Like Embodiment 16, only the weight ratio of marine algal glycoprotein, indigo naturalis, *rhizoma belamcandae* and glucuronic acid is changed as follows:

It comprises 48 portions of marine algal glycoprotein, 9 portions of indigo naturalis, 12 portions of *rhizoma belamcandae* and 13 portions of glucuronic acid by weight.

Embodiment 18

Medicament For Use in Treating Fatty Liver, Hepatitis and Cirrhosis

Like Embodiment 16, only the weight ratio of marine algal glycoprotein, indigo naturalis, *rhizoma belamcandae* and glucuronic acid is changed as follows:

It comprises 99 portions of marine algal glycoprotein, 14 portions of indigo naturalis, 13 portions of *rhizoma belamcandae* and 15 portions of glucuronic acid by weight.

Embodiment 19

Medicament For Use in Treating Fatty Liver, Hepatitis and Cirrhosis

It comprises 1 portions of marine algal glycoprotein, 8 portions of indigo naturalis, 7 portions of *rhizoma belamcandae* and 8 portions of *fructus aurantii* by weight.

The marine algal glycoprotein comprises 41% sugar and 59% protein by weight;
and the molecular weight is 20 kDa;
the marine algae is blue-green algae;
the sugar is a polysaccharide;
the polysaccharide comprises: xylose, fucose, arabinose, glucose, galactose, mannose and rhamnose;
the protein comprises: asparagine, cysteine, lysine, arginine, serine, threonine, glutamic acid.

Embodiment 20

Medicament For Use in Treating Fatty Liver, Hepatitis and Cirrhosis

Like Embodiment 19, only the weight ratio of marine algal glycoprotein, indigo naturalis, *rhizoma belamcandae* and *fructus aurantii* is changed as follows:

It comprises 53 portions of marine algal glycoprotein, 9 portions of indigo naturalis, 8 portions of *rhizoma belamcandae* and 10 portions of *fructus aurantii* by weight.

Embodiment 21

Medicament For Use in Treating Fatty Liver, Hepatitis and Cirrhosis

Like Embodiment 19, only the weight ratio of marine algal glycoprotein, indigo naturalis, *rhizoma belamcandae* and *fructus aurantii* is changed as follows:

It comprises 99 portions of marine algal glycoprotein, 14 portions of indigo naturalis, 13 portions of *rhizoma belamcandae* and 12 portions of *fructus aurantii* by weight.

Application of the medicament in Embodiments 16-21 in treating fatty liver, hepatitis and cirrhosis Using the test method mentioned in Embodiment 7, the medicament has following applicable effects:

TABLE 7

Therapeutic effect of the medicament in the invention on hepatitis

|  | ALT IU/L | TbiL μmol/L | Alb g/L | HBV-DNA Copy/mL | HbeAg Negative conversion rate % | HBV-DNA Negative conversion rate % |
|---|---|---|---|---|---|---|
| Control group before treatment | 77.8 | 60.3 | 31.3 | 5.2 | | |
| Control group after treatment | 41.8 | 38.2 | 34.5 | 4.2 | 70 | 80 |
| Treatment group before treatment | 78.2 | 61.4 | 30.9 | 5.3 | | |
| Embodiment 16 | 34.9 | 32.2 | 34.6 | 3.7 | 80.5 | 87.6 |
| Embodiment 17 | 24.0 | 23.9 | 38.7 | 2.7 | 91.5 | 95.4 |
| Embodiment 18 | 32.5 | 31.5 | 33.6 | 3.6 | 81.4 | 86.4 |
| Embodiment 19 | 32.6 | 30.9 | 35.5 | 3.6 | 82.0 | 86.9 |
| Embodiment 20 | 23.6 | 23.5 | 38.3 | 2.72 | 91.8 | 95.1 |
| Embodiment 21 | 31.9 | 31.9 | 34.2 | 3.59 | 81.4 | 86.6 |

TABLE 8

Therapeutic effect of the medicament in the invention on cirrhosis

|  | ALT IU/L | TbiL μmol/L | Alb g/L | Portal vein diameter (mm) | Splenic vein diameter (mm) | Splenic thickness (mm) |
|---|---|---|---|---|---|---|
| Control group before treatment | 57.8 | 50.3 | 21.3 | 15.8 | 9.2 | 50.5 |
| Control group after treatment | 38.8 | 45.2 | 28.6 | 15.0 | 8.2 | 48.8 |
| Treatment group before treatment | 58.2 | 51.4 | 20.9 | 15.9 | 9.1 | 50 |
| Embodiment 16 | 37.3 | 42.6 | 31.6 | 14.0 | 8.0 | 47.2 |
| Embodiment 17 | 33.6 | 37.0 | 37.6 | 13.5 | 7.5 | 45.2 |
| Embodiment 18 | 37.5 | 42.0 | 32.5 | 14.2 | 8.1 | 47.5 |
| Embodiment 19 | 38.5 | 42.7 | 31.4 | 14.0 | 8.05 | 47.1 |

TABLE 8-continued

Therapeutic effect of the medicament in the invention on cirrhosis

|  | ALT IU/L | TbiL μmol/L | Alb g/L | Portal vein diameter (mm) | Splenic vein diameter (mm) | Splenic thickness (mm) |
|---|---|---|---|---|---|---|
| Embodiment 20 | 33.3 | 36.7 | 37.9 | 13.2 | 7.4 | 44.2 |
| Embodiment 21 | 37.2 | 42.5 | 32.0 | 14.1 | 8.06 | 47.8 |

TABLE 9

Overall curative rate of the medicament in the invention on fatty liver, hepatitis, liver cirrhosis

|  | Markedly effective (rate %) | Effective (rate %) | Ineffective (rate %) | Total effective (rate %) |
|---|---|---|---|---|
| Embodiment 16 | 60.4 | 31.5 | 8.1 | 91.9 |
| Embodiment 17 | 75.6 | 20.0 | 4.4 | 95.6 |
| Embodiment 18 | 65.7 | 26.8 | 7.5 | 92.5 |
| Embodiment 19 | 60.8 | 31.0 | 8.2 | 91.8 |
| Embodiment 20 | 75.7 | 20.7 | 3.6 | 96.4 |
| Embodiment 21 | 60.5 | 30.4 | 9.1 | 90.9 |

In Embodiment 16-18, only the weight ratio of the marine algae glycoprotein, indigo naturalis, *rhizoma belamcandae* and glucuronic acid is changed. From the experimental results, Embodiment 17 is the most preferred embodiment.

In Embodiment 19-21, only the weight ratio of the marine algae glycoprotein, indigo naturalis, *rhizoma belamcandae* and *fructus aurantii* is changed. From the experimental results, Embodiment 20 is the most preferred embodiment.

Embodiment 22

Medicament For Use in Treating Fatty Liver, Hepatitis and Cirrhosis

It comprises, by weight, the following components:
70 portions of marine algae protein, 5 portions of peach kernel, 6 portions of coptis, 7 portions of capillary wormwood herb, 7 portions of manyprickle acanthopanax root, 5 portions of herba inulae and 3 portions of inula flower.

The marine algal glycoprotein comprises 10% sugar and 80% protein by weight.

The molecular weight is 8 kDa;
the glycoproteins in marine algae is the chlorella; the sugar, by weight, comprises the following components: 16 portions of xylose, 12 portions of fucose and 17 portions of arabinose;
the protein mentioned includes the following components: 10 portions of asparagine, 13 portions of cysteine and 19 portions of lysine by weight.

Using the test method mentioned in embodiment 7, the medicament has following applicable effects:

The medicament in the present invention has good therapeutic effect on hepatitis. After 3-month treatment, ALT is 23.3 IU/L, TbiL is 23.0 μmol/L, Alb is 38.2 g/L, HBV-DNA is 2.5 copy/mL, HbeAg negative rate is 92.3% and HBV-DNA negative rate is 95.6%.

The medicament in the invention has good therapeutic effect on liver cirrhosis. After 3-month treatment, ALT is 33.0IU/L, TbiL is 36.2 μmol/L, Alb is 38.6 g/L, portal vein diameter is 13.0 mm, splenic vein diameter is 7.4 mm and spleen thickness is to 45.2 mm.

The medicament in the invention has high curative rate in treating of liver cirrhosis with markedly effective rate is 70%, effective rate is 26.4%, ineffective rate is 3.6% and total effective rate is 96.4%.

Embodiment 23

Preparation Method of Medicament For Use in Treating Fatty Liver, Hepatitis and Cirrhosis Including the Following Steps:

(1) weighing measuring according to prescriptive;
(2) Washing of Traditional Chinese Medicine washing and cleaning all Chinese herbal medicines excluded marine algae protein;
(3) extraction of traditional Chinese medicine adding 12 times volume water into the tradition Chinese medicines mixture and let it soak for 1h at temperature of 50° C.; then increase the temperature to 60° C. and 20 kPa pressure applied, extract auxiliarilly with ultrasound whose power is 130 w and frequency is 250 kHz.Treat it 4-5 s at interval of 2-6 s. 1h later, filter the mixture, collect fluid and dry with mist spray to make TCM powder;
(4) Adding Qlycoprotein
mixing the powder of glycoprotein in marine algae with the above powder of traditional Chinese medicine to produce different dosage forms such as capsules and tablets.

For the medicament mentioned in this invention, pH is between 5.3-9.8 and 6.5-7.5 is preferred.

The invention has been subjected to a large number of experiments, and we have carried out multiple tests using a mixture of marine shells, bones of livestock and poultry, a mixture of glycoprotein, polysaccharides and proteins extracted from the skeleton of marine animals, and the objectives of the invention have also been achieved.

Embodiment 24

Medicament or Use in Treating Fatty liver, Hepatitis and Cirrhosis

The medicament is a mixture of polysaccharides and proteins;
the medicament comprises 1%-99% of polysaccharide and 1%-99% of protein by weight; the polysaccharide comprises: xylose, fucose, arabinose, glucose, galactose, mannose and rhamnose;
the protein mentioned includes: Asparagine, cysteine, lysine, arginine, serine, threonine, alanine, aspartic acid, glutamine, glutamic acid, histidine, isoleucine, glycine, leucine, methionine, phenylalanine, valine, tyrosine, and valine;
as for the mixture of polysaccharide and the protein, the polysaccharide has a molecular weight of 0.2-3000 kDa and the protein has a molecular weight of 0.2-3000 kDa.

The mixture of polysaccharides and proteins, further a mixture of algal polysaccharides and algal proteins;

the mixture of the algal polysaccharide and the algal protein also comprises a pigment;

the pigment is a natural pigment contained in the algal substance; the algal protein may be phycocyanin, phycoerythrin or algae xanthoprotein.

The glycoprotein includes synthetic glycoprotein, synthetic polysaccharide and protein.

The medicament hereof has a No Observed Adverse Effect Level (NOAEL) of 1.6 g/kg for 12-week oral administration for dogs, which is equivalent to 50 times the equivalent dose for humans, so it is concluded that the safety of the clinical trial can be guaranteed.

The medicine described in the present invention can also be a health care product or a food.

The basic principles and main features of the present invention and the advantages of the present invention are shown and described above. It should be understood by the technicians in this field that, the present invention is not limited by the foregoing embodiments, and that what are described in the aforementioned embodiments and instructions are only the principles of this invention; without departing from the spirit and scope of the invention, this invention may be subject to various changes and modifications, which will be included within the scope of the invention as claimed. The scope of the invention is defined by the appended claims and their equivalents.

What is claimed is:

1. A medicament for use in treating fatty liver, hepatitis and cirrhosis, wherein the medicament comprises: a glycoprotein, indigo naturalis, and glucuronic acid in a ratio of 53:8:14 by weight, wherein the glycoprotein is a marine algal glycoprotein and the marine algal glycoprotein is obtained from *chlorella*, the glycoprotein has a molecular weight of 35 kDa, and the medicament is in a form of a capsule or a tablet.

* * * * *